US00PP33246P3

(12) United States Plant Patent
Bost

(10) Patent No.: US PP33,246 P3
(45) Date of Patent: Jul. 13, 2021

(54) OZARK CHESTNUT TREE NAMED 'OZ HUNTER'

(50) Latin Name: *Castanea ozarkensis*
Varietal Denomination: Oz Hunter

(71) Applicant: Stephen H. Bost, Poplar Bluff, MO (US)

(72) Inventor: Stephen H. Bost, Poplar Bluff, MO (US)

( * ) Notice: Subject to any disclaimer, the term of this patent is extended or adjusted under 35 U.S.C. 154(b) by 0 days.

(21) Appl. No.: 16/873,460

(22) Filed: Apr. 16, 2020

(65) Prior Publication Data

US 2020/0337190 P1 Oct. 22, 2020

Related U.S. Application Data

(60) Provisional application No. 62/836,082, filed on Apr. 19, 2019.

(51) Int. Cl.
*A01H 5/08* (2018.01)
*A01H 6/54* (2018.01)
*A01H 6/00* (2018.01)

(52) U.S. Cl.
USPC ..... Plt./152
CPC ..... *A01H 6/00* (2018.05); *A01H 5/08* (2013.01)

(58) Field of Classification Search
USPC ..... Plt./152
CPC ... A01H 5/08; A01H 5/00; A01H 6/00; A01H 6/54; A01H 5/02
See application file for complete search history.

(56) References Cited

PUBLICATIONS

International Code of Nomenclature for Cultivated Plants 2016 Ninth edition, cover page, pp. 28-30. (Year: 2016).*

* cited by examiner

*Primary Examiner* — June Hwu
(74) *Attorney, Agent, or Firm* — Antoinette M. Tease

(57) ABSTRACT

'Oz Hunter' is a new and distinct North American *Castanea* cultivar that is blight-resistant, precocious and a producer of heavy annual crops of one to six nuts per bur. It produces a heavy crop of nuts each year with a small-sized nut containing the highest protein and carbohydrate percent of any chestnut. Nut drop begins around September 10 and continues for a seven- to eight-week period. Most of the nuts produced drop in the first five weeks of the period of nut drop from this cultivar. 'Oz Hunter' is a medium-sized tree that has an elliptic-shaped canopy with high upright to spreading and diffuse lateral branches. This ten-year-old cultivar is 7.92 meters tall with a canopy covering an area 21.22 square meters. Its heavy nut crop occurs from early September through mid-November, providing the highest protein and carbohydrate nut crop of any chestnut for people and wildlife.

11 Drawing Sheets

Latin name: *Castanea ozarkensis*.
Varietal denomination: 'Oz Hunter'.

BACKGROUND OF THE INVENTION

The genus *Castanea* includes the Ozark chinquapin, the American chestnut and the Allegheny chinkapin. Over three billion trees from the genus *Castanea* have been lost in North American due to the chestnut blight *Cryphonectria parasitica*. The blight was accidentally imported on chestnut trees from Asia and was first noticed in New York City in 1904. The blight spread quickly killing trees by the fungus entering the bark and killing the cambium of the tree, cutting off vital nutrients. By the 1940s the chestnut blight *Cryphonectria parasitica* had reached the west side of the Mississippi River and began killing millions of Ozark chinquapin trees.

Before the arrival of the chestnut blight, the Ozark chinquapin was an abundant forest tree that provided a dependable high-protein nut crop every year without fail, and this crop was a very important food source for people and wildlife. The loss of this tree also had a negative impact on forest ecosystems that depended on it. The blight kill was so devastating that it was thought that no Ozark chinquapin tree had survived.

The object of the present invention is to provide an Ozark chinquapin tree that is resistant to the chestnut blight, has a high-yield nut crop and is fast-growing. This newly created cultivar is a dependable high-protein food source and an economic resource for people. This new cultivar will be a dependable food source for wildlife that is not present in forest today. Forest ecosystems will also benefit from this blight-resistant cultivar.

The present invention is the result of over fourteen years of field and laboratory research. This work has included hundreds of emails and calls networking with farmers, thousands of miles driven and rigorous hiking in rough terrain on a mission to discover surviving trees that exhibited some levels of blight resistance. This search encompassed seven states, and in February 2006, the inventor discovered the first tree that had not died of the blight. Other discoveries followed, and the inventor began collecting genetic material for a breeding program to enhance this desired trait. These trees were carefully selected from thousands of trees found in Missouri, Arkansas, Louisiana, Oklahoma, Texas, Mississippi and Alabama.

In the fall of 2006, remote locations for research test plots were established in Carter, Shannon, Dent and Cape Girardeau counties in Missouri. These sites were selected because they had well-drained soils, were in secure locations to minimize vandalism, and had diverse plant populations and wildlife in immediate proximity. These requirements needed to be met to assure that these trees could be established in similar historic locations with minimal care and thrive.

Another important consideration for the breeding program was monitoring how 'Oz Hunter' could coexist with new threats that were not an issue 80 years ago. Today, resistance to the chestnut blight is the greatest threat to 'Oz Hunter' survival; however, new diseases, pathogens and invasive insects and plants are also threatening agriculture and forest ecosystems. For example, Ink Disease *Phytophthora cinnamomi*. is present in the soils, and invasive species of Gall Wasp and leaf-eating Asiatic Oak Weevils have wreaked havoc for the last two decades on recovery efforts of the American chestnut.

Beginning in 2007 genetic material from these carefully selected trees was planted on research test plots. Further controlled pollination were conducted to increase blight resistance and produce higher nut yields and faster growth. This process has resulted in a cultivar with traits not found in wild Ozark chinquapin trees; the present invention is resistant to the chestnut blight and will produce up to six nuts per bur, making it multiple times more productive than wild cultivars. With double production not uncommon with this new cultivar, is precocious, growing 15% to 45% faster than wild Ozark chinquapin trees without fertilizer or soil amendments.

'Oz Hunter' is the product of a controlled pollination of two promising parent trees growing at the Hunter Mo. research plot: "R-20X" (male parent) and "R-17" ( female parent ), whose origins are Missouri and Arkansas, respectively. Controlled pollination created a single viable nut ('Oz Hunter'), which was directly planted on the same plot west of Hunter, Mo., where the parents were growing. The present invention relates to a newly created and distinct Ozark chinquapin cultivar that has high blight resistance, produces more than one nut per bur, and has a rapid growth rate. Stems from 'Oz Hunter' were grafted onto Chinese chestnut root stock in 2012, 2013, 2018 and 2020 in Hunter, Mo. Observations of these clones demonstrated uniform, stable and consistent characteristics of claimed cultivar. The claimed plant was created by the inventor on remote research test plots west of Hunter, Mo., and pollen was collected from select trees on the research test plots. Both parent trees of 'Oz Hunter' died from chestnut blight and produced only a single nut per bur. The claimed plant has high resistance to the chestnut blight and produces multiple nuts per bur as well as single nuts per bur. 'Oz Hunter' is ten years old.

BRIEF SUMMARY OF THE INVENTION

The present invention relates to a new and distinct Ozark chinquapin cultivar that is blight-resistant and highly productive. This new cultivar produces large nut crops of one to six nuts per bur, has the highest percentage of protein and carbohydrates of any chestnut, and was created by using stem grafts and controlled pollination. This method is still being used today on research test plots in Carter, Shannon, Dent and Cape Girardeau counties in Missouri.

BRIEF DESCRIPTION OF THE PHOTOGRAPHS

DETAILED BOTANICAL DESCRIPTION

A. Overview

Figure 1:
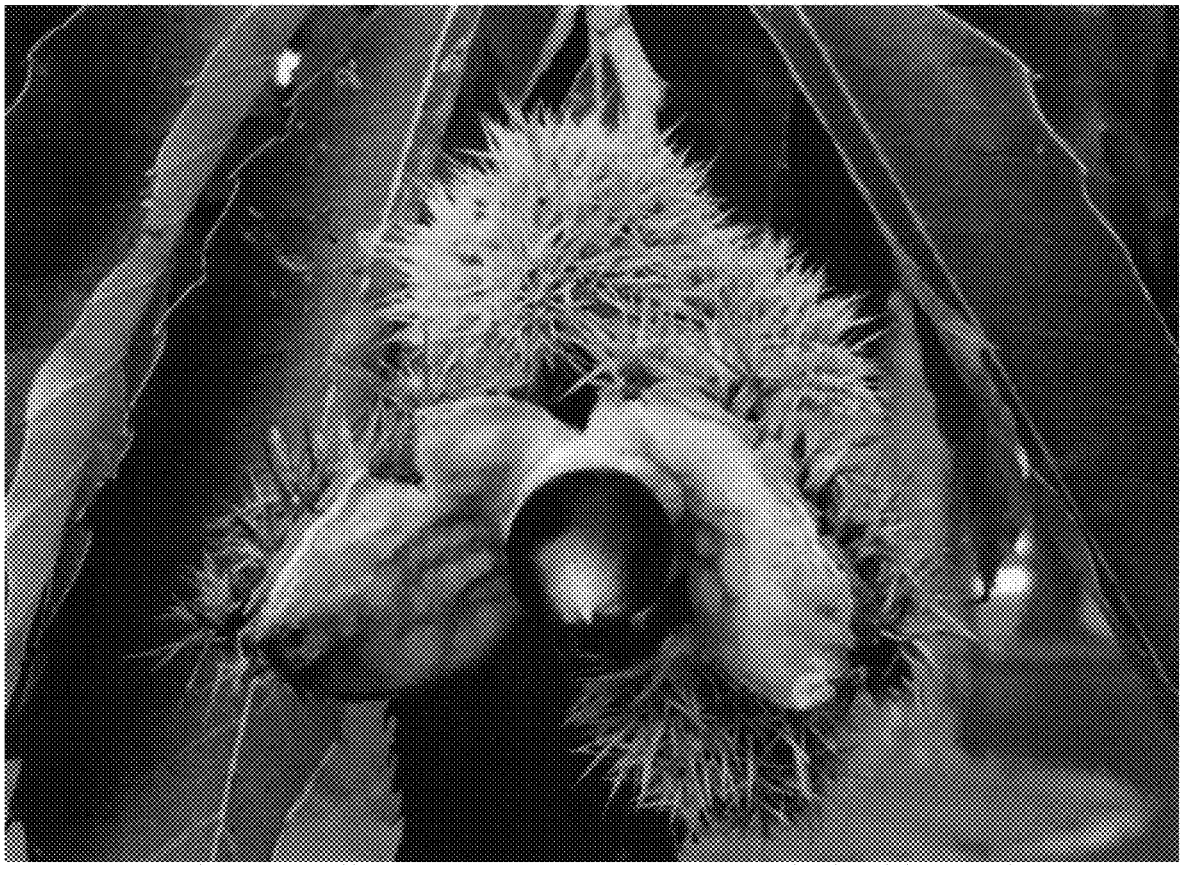
FIG. 1 is a photograph of wild Ozark chinquapin with only one nut per bur that splits into two equal halves.

The present invention, 'Oz Hunter', is the product of a controlled pollination of two promising parent trees growing at the Hunter, Mo. research plot: "R-20X" (male parent) and "R-17" (female parent), whose origins are Missouri and Arkansas, respectively. Controlled pollination created a single viable seed ('Oz Hunter'), which was directly planted on the same plot west of Hunter, Mo., where the parents were growing. The present invention relates to a newly created and distinct Ozark chinquapin cultivar that is blight-resistant and produces more than one nut per bur. Grafts from 'Oz Hunter' stems onto Chinese chestnut root stock were done in 2012, 2013, 2018 and 2020. Observations of the clones were uniform and consistent with characteristics of claimed cultivar. The resistance of 'Oz Hunter' to chestnut blight was confirmed through a series of detached leaf assays, a method of screening trees for blight tolerance through inoculation.[1] Blight resistance of 'Oz Hunter' was also confirmed by an oxalate assay, which measures oxalate activity in plant tissue.[2] These laboratory findings, along with field trials, demonstrate a superior blight resistance of the new cultivar created. The claimed invention prefers USDA Plant Hardiness Zone 5-8.

The Ozark chinquapin, *Castanea ozarkensis*, is a species native to North America that will grow between 25° and 45° North latitudes. Labratory DNA studies indicate it has a more diverse gene pattern than the American chestnut or the Alleghany chinkapin and is the oldest *Castanea* in North America. The Ozark chinquapin is more resistant to chestnut blight *Cryphonectria parasitica* than the American chestnut

*Castanea dentata* and less blight-resistant than the Chinese chestnut *Castanea mollissima*. Ozark chinquapins grow in soils that are low in organic material and are well-drained. The tap root of this tree serves as a survival mechanism in the first decade of life, allowing the tree to survive drought and extreme summer temperatures. These trees grow in acidic soils with PH 5.2-6.5. The name "chinquapin" is an Algonquin Indian word that translates to "little tasty chestnut." Historic records from survey notes, newspaper articles, pollen analysis, recent discoveries of remnant populations and modern DNA testing verify that the Ozark chinquapin tree had a native range that extended from Texas and Oklahoma, through Georgia and into Virginia.

When the trees are young, the bark is smooth with a brown to gray color that resembles applewood. As the tree matures, the bark becomes long and deeply furrowed. Trees can grow to 24 meters tall and up to one-meter diameter at breast height (DBH) with deep saw-toothed leaves of a deep green with a silver cream color on the underside. In the fall, the leaves turn yellow before becoming brown and falling from the tree. On blighted stump sprouts, the dead leaves tend to cling to the branches through the winter. The leaves are often slightly wider in the middle; however, leaves on the same tree will have a narrower chestnut-like appearance. The pellicle or thin membranous skin on the nuts is thin and peels readily from the kernel. Trees are a spreading type in full sun with more of a vase shape as the tree matures, reaching a height of 25 meters. This is a medium age lived tree averaging 70-110 years. The trees will sometimes sprout one and sometimes two stems from the base of the tree. This phenomenon was also common in pre-blighted forest.

Ozark chinquapins are monoecious and cannot self-pollinate, requiring another pollinator. Staminate flowers appear on erect cylindrical catkins with 4-16 stamens. It is not uncommon on this new cultivar to produce nuts in the third year of growth. This new cultivar can produce catkins of staminate flowers the second year of growth. This cultivar can produce nuts the third year of growth by production of pistillate flowers. Nuts are small and chestnut brown in color. 'Oz Hunter' produces not just one nut per bur but typically two to six nuts per bur. Approximately 20% of burs produce multiple nuts and approximately 80% of burs produce a single nut. The burs that produce multiple nuts are approximately 25% larger than burs produce a single nut.

'Oz Hunter' is a medium-sized tree that is broadly elliptic in shape with high, upright and horizontal spreading branches. The 'Oz Hunter' tree is a ten-year-old tree 7.92 meters tall with a trunk diameter of 19.5 cm. The canopy is 5.18 meters wide with a canopy area of 21.22 sq. meters and potential maturity height of 15-20 meters.

'Oz Hunter' produces a large nut crop every year. The nuts start dropping about September 10 and continue to drop for a seven- to eight-week period. A high percentage of the nuts produced by this cultivar drop during the first five weeks of the nuts' drop. 'Oz Hunter' is a medium sized tree that is blight-resistant, precocious, and produced one to six nuts per bur. These nuts are extremely high in protein and carbohydrates. The tree fruits annually and produces a large nut crop for the tree size. It also drops the nuts over an extended time period.

'Oz Hunter' ships extremely well, with a fruit storage life in the right conditions of one to three years. At one time the Ozark Chinquapin was a dependable food source. The potential market uses are high, especially with snack food industry, organic and healthy diet market. In terms of the productivity of fruit, a 7.9 meters tall tree producing 6.000 nuts is equivalent to 0.48 kilograms nut weight/421.8 kilograms estimated plant weight with 19% error (see below calculations for a comparable size white oak).

Comparable sized White Oak—Multiply the green above ground weight×2 equals weight of roots. Total green weight of tree is total of roots and above ground weight. Standard error estimated as percentage of predicted mean is 19%. 310 pounds green above ground weight×2=620 root weight. 310+620=930 est. pounds=421.8 kilograms.

In 2018 at research test plots in Carter County, Mo. 'Oz Hunter' was checked for nut production. Carefully counting nuts collected each Tuesday for seven weeks yielded a total of 3,844 nuts collected. This yield is over twice the production of a same size wild Ozark chinquapin; however, trail camera pictures and videos indicated many more nuts than the 3,844 were produced but eaten by wildlife, including deer, turkeys, raccoons, squirrels, chipmunks, packrats, mice, voles, blue jays, woodpeckers and shrews, before they could be collected and counted. The true number produce is estimated to be approximately 6,000 nuts. This new cultivar could become an important food source for people, wildlife, and domestic livestock and may be used in agroforestry, wildlife food plots and orchards.

In 2006 the inventor discovered a rare Ozark chinquapin tree along the edge of a cultivated farm field in south west Arkansas that exhibited levels of blight resistance and was used to help create 'Oz Hunter'. During the search tor surviving trees that might have blight resistance, more than 2,700 blighted Ozark chinquapin sprouts, stump sprouts, saplings, hybrids, Alleghany chinkapin, American chestnut and look-alike trees were observed in the field before the inventor carefully selected Ozark chinquapin trees that exhibited levels of blight resistance. Laboratory DNA tests were performed starting in 2007 to confirm that the trees being used in the breeding program were pure Ozark chinquapin trees that were not hybridized with any foreign or domestic *Castanea*. From this group of selected Ozark chinquapin trees that exhibited levels of blight resistance, the number was narrowed down further by removing trees that exhibited undesirable traits such as low nut production, smaller than average size of nuts, slower growth rate and later sexual maturity. Repeated controlled pollination yielded desirable traits that were consistent and present in F1 generations. Continued field observations and laboratory blight testing confirm F2 generations were also consistent with the same desirable traits.

In February 2007 the inventor nut grafted stems from the first tree he discovered in southwest Arkansas bordering the cultivated farm field, collecting pollen from these clones the same year. The pollen was dried and frozen at −18 C to be used later. In 2006 along a roadway in rural southwest Missouri the inventor discovered a unique Ozark chinquapin growing along a rural road by an orchard and large garden. The tree, unlike others he had discovered, had a large branch cut away from it by the rural electric coop and was not reacting to the blight as other trees the inventor had observed. Like the first tree found in southwest Arkansas, this tree exhibited levels of resistance to the blight. The inventor returned in late May 2007 and carefully pollinated the tree with the landowner's permission. The pollen used was collected from nut-grafts done with the tree from southwest Arkansas. He collected approximately 20 seeds from this controlled cross. In the spring of 2008 these crosses were planted on research test plots that were previously established. In 2010 the inventor collected pollen from these trees that demonstrated desired traits. Pollen from these select trees was then crossed with yet another controlled cross that demonstrated fast, vigorous growth, produced pollen in the second year and exhibited no indications of blight. Clones made with grafts from these trees and seed planted from them were carefully observed for the next three seasons. Careful controlled pollination of these trees continued, and more grafts were created to check the consistency of F1 and F2 generations. Desirable traits pertaining to high yield, multiple nuts per bur, and rapid growth were observed in the field, and laboratory tests confirmed high consistent blight resistance in F1 and F2 generations. Cloning with stem grafts, controlled pollination, planting seed from the cultivar and testing continue today for monitoring of desirable traits.

The two charts provided immediately below illustrate the specific differences between the new cultivar 'Oz Hunter' and natural occurring wild populations of Ozark chinquapin. The present descriptions pertain to the variety as grown on research test plots in Carter, Shannon, Dent and Cape Girardeau counties in Missouri.

CHARACTERISTICS NEW VARIETY

Tree:

*Size*.—Small — 7.92 meters tall with a canopy width of 5.18 meters and a canopy area of 21.22 sq. meters, potential maturity mature height of 15-20 meters. Tree shape is broadly elliptic becoming vase like as it matures.

*Vigor*.—Vigorous.

Trunk:

*Form*.—Upright with branches high and diffuse as well as extended lateral spread, subbasicaulous common.

*Texture*.—Relatively smooth when young becoming deep furrowed in long strips as it matures.

*Color of bark*.—Brown or gray, becoming grayer as it matures.

Branches:

*Form*.—Upright to spreading.

*Texture*.—Relatively smooth.

*Lenticels*.—Few, small, 34 per square centimeter, oval in shape.

*Branching habit*.—Horizonal spreading as well as lateral high and diffuse.

*Color*.—New wood grey-brown, with grey as it matures.

Foliage:

*Quantity*.—Abundant.

*Density*.—Dense.

Leaves:

*Size*.—Varies from 16-27 cm.

*Width*.—Varies from 5-8 cm.

*Leaf ratio*.—1.7-2.2.

*Shape*.—Elliptical.

*Leaf tip*.—Acute.

*Leaf base*.—Narrowly rounded or wedge shaped, sometimes subobtuse.

*Leaf arrangement*.—Alternate.

*Leaf bud*.—Average size of bud is 4-5 millimeters diameter, 7-9 millimeters long, round in cross section, ovoid shaped, two imbricate bud scales, pubescence, blunt buds, 26- to 48-degree angle to stem. Leaf bud burst varies greatly with aspect, elevation, and hours of sunlight. In USDA Zone 6a, it occurs mid- to late April.

*Leaf stipules*.—Pair of lateral leaf stipules attached at either side of leaf base, point away from stem at 74-degree angle, curved shape pointing back away from stem, average 11 millimeters long, one millimeter wide at base gradually tapering to point at the end. Classification is persistence and fall off in June.

*Thickness*.—Thin, leaf venation pinnate, moderately prominent abaxially.

*Texture of adaxial*.—Coriaceous.

*Texture of abaxial*.—Pubescent with short downy erect hairs visible under magnification.

*Margin*.—Deeply serrated saw-toothed.

*Petiole*.—Length 1.0 cm-1.4 cm.

*Petiole pubescence*.—Glabrous to sparsely simple hairs.

*Color*.—Adaxial surface deep green low luster, glabrous blade, abaxial silvery cream surface, under magnification moderately to densely stellate hairs on blade.

Bloom:

*Amount of bloom*.—Heavy.

*Color*.—Green changing to yellow then cream during 2-3 days of pollination.

*Blooming period*.—Late May to early June.

*Age at which tree starts flowering*.—Early, first year for grafts, 2-3 years for planted nuts.

*Male flower*.—Catkin length 10-18 cm.

*Male flower*.—Stamen number per catkin 4-16.

*Female flower*.—Flower number per bur 1-6.

*Female flower*.—Style number per flower 4-7.

*Female flower*.—Average size of female flower is 5.4 millimeters diameter and 9.3 millimeters length.

Crop:

*Bearing*.—Regular annual bearer.

*Productivity*.—Prolific.

*Ripening period*.—Long, nuts begins dropping approx. September 10 and continue for a 7-8-week period.

*Distribution of nuts on tree*.—Well distributed, fruits 16-28 cm from the terminals with 6-47 burs.

*Tenacity*.—Burs crack while on tree and nuts release and drop from bur.

Hull:

*Description*.—Spiny round bur, splits into two halves if one nut splits into four equal parts if 2-6 nuts occur.

*Size*.—3.8-4.2 cm in diameter for single nut, 3.5-5.5 cm for burs with 2-6 nuts.

*Number of nuts per bur*.—1-6 per bur.

*Dehiscence*.—Splits easily when still on tree.

*Color*.—Yellow-green-tan at dehiscence.

Nut:

*Size*.—Small.

*Average size*.—1.55 cm×1.72 cm for single round nut, 0.85 cm×0.87 cm×1.72 cm for 2-6 nuts per bur.

*Average weight*.—0.8 grams per nut, 567 nuts per pound.

*Form*.—Round, and others flattened on 2 side with 3-6 nuts, occ. 2, hemispheric to somewhat ovoid on other side.

*Blossom end*.—Broadly rounded with an obtuse tip.

*Basal end*.—Broadly rounded to flat.

*Color*.—Chestnut brown.

*Pubescence*.—Glabrate; nut is glossy and smooth with no pubescence, exception being pointed tip end of nut opposite hilium is pubescent.
*Area of hilium*.—Medium.
*Conspicuousness of hilium*.—Conspicuous.
*Glossiness of hilium*.—Absent.
*Shell*.—Thin.
*Hardness of shell*.—Relatively hard, yet not rigid.
*Texture of shell*.—Smooth.
*Percentage of kernel to nut*.—Very high +95%.

Bur:
*Shape*.—Egg shaped, pointed opposite of base.
*Density*.—Very dense.

Kernel:
*Size*.—Almost as large as nut size.
*Form*.—Same as nut shape.
*Pellicle*.—Thin, tan in color.
*Flavor*.—Excellent, very sweet.
*Color*.—Light-straw to tan.

Seeds:
*Seed coat adherence*.—Medium.

Resistance to insects: Trees less than 3 meters tall experience leaf damage from Asiatic oak weevils *Cyrtepistomus castaneus*. Resistant to Oriental chestnut gall wasp *Dryocosmus kuriphilus*.

Resistance to disease: Two laboratory tests confirm high resistance to chestnut blight *Cryphonectria parasitica*. Resistant to Ink Disease *Phytophthora cinnamomi*. Nut damage from Small Chestnut Weevils *Curcullio sayi*.

Mammal damage: Bark of trunks are damaged by the antlers of white tail deer, rabbits gnaw the bark of young trees in winter, and black bears break limbs and damage bark. Deer, bear, squirrels, voles, rabbits, mice, packrats, chipmunks and variety of birds eat the nuts.

The color description of the claimed invention is further described as follows: Inventor used The Royal Horticultural Society Colour Chart, Sixth Edition 2015, for the following color descriptions of listed botanical features.

*Bark*.—When young bark is smooth with two colors combinations produced, RHS N199 D Strong Yellowish Brown, and a second color pattern, which consists of a mixture of two irregular, randomly shaped blotches of RHS 202 D Light Greenish Grey and RHS 202 C Greenish Grey. As the tree matures, the bark changes from smooth surface to deeply furrowed with long ridges of bark. Tops of bark ridges are RHS 156 D Yellowish White, and furrows are RHS 202 B Medium Grey.
*Leaves*.—Adaxial — RHS 140 A Vivid Yellowish Green and Abaxial — RHS NN155 A Yellowish White.
*Branches*.—Two colors observed: RHS N199 C Moderate Yellowish Brown and RHS 201 D Pinkish Grey.
*Petiole*.—RHS 150 C Brilliant Yellow.
*Stent*.—Two colors observed: RHS NT99 C Moderate Yellowish Brown and RHS 201 D Pinkish Grey.
*Male catkins*.—RHS 155 B Yellowish White.
*Female flowers*.—RHS 140 C Brilliant Yellowish Green.
*Bur prickles*.—During bur split color is RHS 154 B Brilliant Yellow Green, changing to RHS 174 C Reddish Greyish Orange after bur fully opened and nut falls from bur.
*Nut*.—RHS 200 A Dark Greyish Reddish Brown.
*Kernel*.—RHS NN155 B White.
*Lenticel*.—RHS NN155 C White.
*Leaf bud*.—RHS 175 C Dark Reddish Grange.
*Leaf stipules*.—RHS 140 C Brilliant Yellowish Green.
*Female flower*.—RHS 140 C Brilliant Yellowish Green.

CHARACTERISTICS WILD VARIETY OZARK CHINQUAPIN

Tree:
*Size*.—Small tree or shrub like status, primary occurrence in form of blighted stump sprouts — rarely reaching height great than 5 meters because of cyclic chestnut blight kill. Tree shape is shrubby to varies stages of blight killed stems.
*Vigor*.—Moderately vigorous.

Trunk:
*Form*.—Dead stump visible in absence of fire, subbasicaulous blighted stump sprouts, extremely rare to find tree form.
*Texture*.—Relatively smooth when young, rarely growing to becoming deep furrowed in long strips as it matures.
*Color of bark*.—Brown or gray, becoming grayer as it matures.

Branches:
*Form*.—Upright to spreading.
*Texture*.—Relatively smooth.
*Lenticels*.—Few, small.
*Branching habit*.—Horizonal spreading as well as lateral high and diffuse.
*Color*.—New wood grey-brown, with grey as it matures.

Foliage:
*Quantity*.—Minimal.
*Density*.—Minimal.

Leaves:
*Size*.—Varies from 16-27 cm.
*Width*.—Varies from 5-8 cm.
*Leaf ratio*.—0.6-1.1.
*Shape*.—Elliptical in closed canopy, spreading in open canopy.
*Leaf tip*.—Acute.
*Leaf base*.—Narrowly rounded or wedge-shaped sometimes subobtuse.
*Leaf arrangement*.—Alternate.
*Leaf bud*.—Average size of bud is 4-5 millimeters diameter, 7-9 millimeters long, round in cross section, ovoid shaped, two imbricate bud scales, pubescence, blunt buds, 26- to 48-degree angle to stem. Leaf bud burst varies greatly with aspect, elevation, and hours of sunlight. In USDA Zone 6a, it occurs mid- to late April.
*Leaf stipules*.—Pair of lateral leaf stipules attached at either side of leaf base, point away from stem at 74-degree angle, curved shape pointing back away from stem, average 11 millimeters long, one millimeter wide at base gradually tapering to point at the end. Classification is persistence and fall off in June.
*Thickness*.—Thin, leaf venation pinnate, moderately prominent abaxially.
*Texture of adaxial*.—Coriaceous.
*Texture of abaxial*.—Pubescent with short downy erect hairs visible under magnification.

*Margin.*—12 to 25 deeply serrated saw-toothed.
*Petiole.*—Length 1.0 cm-1.4 cm.
*Petiole pubescence.*—Glabrous to sparsely simple hairs.
*Color.*—Adaxial surface deep green low luster, glabrous blade, abaxial silvery cream surface, under magnification moderately to densely stellate hairs on blade.

Bloom:
*Amount of bloom.*—Minimal or nonexistent in closed canopy, minimal to moderately heavy in open canopy.
*Color.*—Changing to yellow then cream during 2-3 days of pollination.
*Blooming period.*—Late May to early June.
*Age at which tree starts flowering.*—Nonexistent to 4-7 years.
*Male flower.*—Catkin length 10-18 cm.
*Male flower.*—Stamen number per catkin 4-16.
*Female flower.*—Flower number per bur 1.
*Female flower.*—Style number per flower 4-7.
*Female flower.*—Average size of female flower is 5.4 millimeters diameter and 9.3 millimeters length.

Crop:
*Bearing.*—Historically an annual bearer, today almost nonexistent.
*Productivity.*—Nonexistent to rare, monoecious needing another pollinator, wildlife predation further limits viable seed base.
*Ripening period.*—Nonexistent to sporadic, nuts begins dropping approx. September 10 to October 15.
*Distribution of nuts on tree.*—Nonexistent to sparse, if present usually on upper branches.
*Tenacity.*—Burs crack while on tree and nuts release and drop from bur.

Hull:
*Description.*—Spiny round bur.
*Size.*—3.8-4.2 cm in diameter for single nut.
*Number of nuts per bur.*—1 nut per bur.
*Dehiscence.*—Splits easily when still on tree.
*Color.*—Yellow-green-tan at dehiscence, non-viable burs on tree prematurely turn brown.

Nut:
*Size.*—Small.
*Average size.*—1.55 cm×1.72 cm for single round nut.
*Average weight.*—0.8 grams per nut, 567 nuts per pound.
*Form.*—Round.
*Blossom end.*—Broadly rounded with an obtuse tip.
*Basal end.*—Broadly rounded to flat.
*Color.*—Chestnut brown.
*Pubescence.*—Glabrate; nut is glossy and smooth with no pubescence, exception being pointed tip end of nut opposite hilum is pubescent.
*Area of hilium.*—Medium.
*Conspicuousness of hilium.*—Conspicuous.
*Glossiness of hilium.*—Absent.
*Shell.*—Thin.
*Hardness of shell.*—Relatively hard, yet not rigid.
*Texture of shell.*—Smooth.
*Percentage of kernel to nut.*—Very high +95%.

Bur:
*Shape.*—Egg shaped, pointed opposite of base.
*Density.*—Very dense.

Kernel:
*Size.*—Almost as large as nut size.
*Form.*—Same as nut shape.
*Pellicle.*—Thin, tan color.
*Flavor.*—Excellent, very sweet.
*Color.*—Light-straw to tan.

Seeds:
*Seed coat adherence.*—Medium.

Resistance to insects: Trees less than 3 meters tall, leaf defoliation high from Asiatic oak weevils *Cyrtepistomus castaneus*. Resistant to Oriental chestnut gall wasp *Dryocosmus kurlphilus*.

Resistance to disease: Chestnut blight *Cryphonectria parasitica*, has decimated populations to the point tree has an S2 state rank in Missouri as critically imperiled species of concern. Resistant to Ink Disease *Phytophthora cinnamomi*. Nut damage from Small Chestnut Weevils *Curculio sayi*.

Mammal damage: Bark of trunks are damaged by the antlers of white tail deer, rabbits gnaw the bark of young trees in winter, and black bears break limbs and damage bark. Deer, bear, squirrels, voles, rabbits, mice, packrats chipmunks and variety of birds eat nuts.

'Oz Hunter' is distinguished from wild Ozark chinquapins in several ways. For example, it is blight-resistant, will live as a tree 15 to 20 meters tall, produces more than one nut per bur, produces burs that split into four equal quarters, and has high nut production and accelerated growth rate. Wild Ozark chinquapin trees will eventually die of the chestnut blight or survive as a bush of blighted stump sprouts less than four meters tall because they have low resistance to the chestnut blight; they also produce only a single nut from a bur that splits into two equal halves, have low nut production, and a slower growth rate. The described wild Ozark chinquapin is the closest known variety to the inventor.

Leaf assay tests conducted at the Missouri Botanical Garden Laboratory confirmed that F1 and F2 successive grafted generations from 'Oz Hunter' demonstrated same claimed same traits as 'Oz Hunter' parent tree. Clones of F1 generations of 'Oz Hunter' were verified as high blight resistance using oxalate assay test conducted at the Syracuse, N.Y., College of Environmental Science and Forestry laboratory in 2019. The current season's shoot thickness and internode length are both medium.

B. Detailed Description of the Figures

FIG. 1 is a photo of an Ozark chinquapin one would observe in the wild, with only one nut per spiky bur and the bur splitting into two equal halves as the nut ripens. The term chinquapin or chinkapin refers to a tree or bush that produces only one round nut per bur with the bur splitting into two equal halves as the nut ripens.

Figure 2:
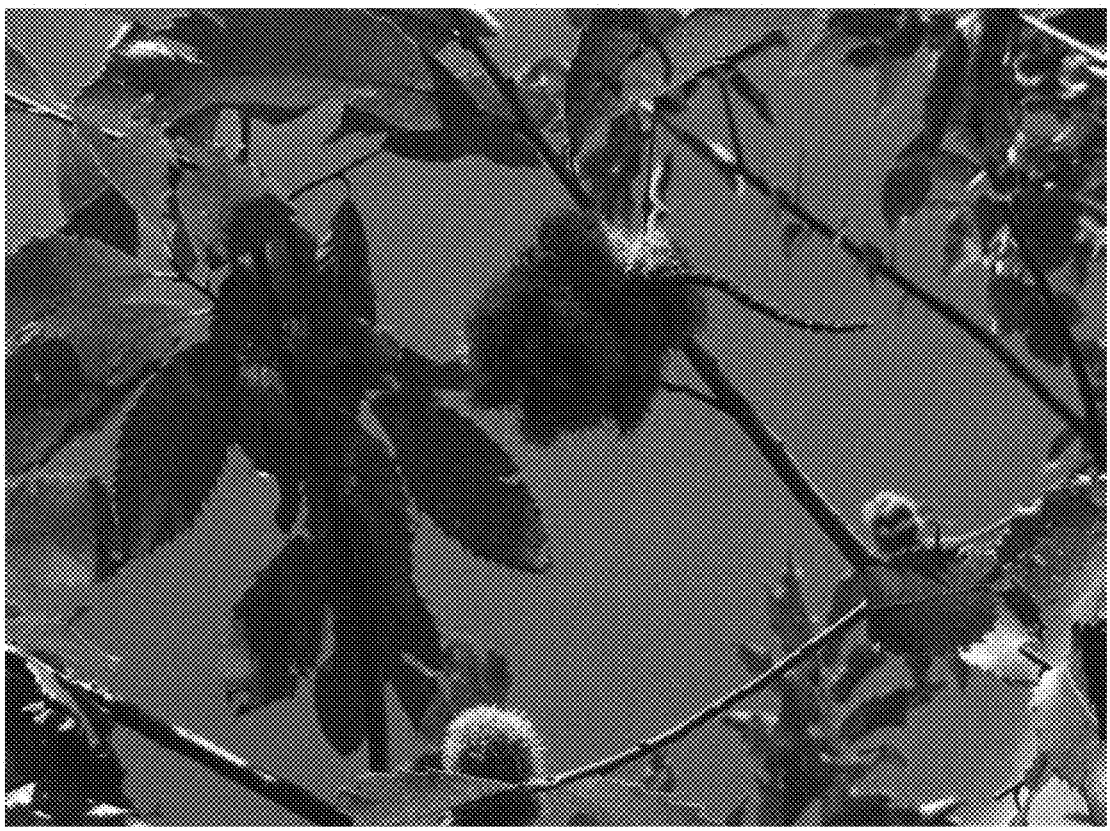
FIG. 2 is a photograph of 'Oz Hunter' with two to six nuts per bur with the bur splitting into four equal parts.

FIG. 2 is an example of 'Oz Hunter' producing multiple two to six nuts per spiky bur with the bur splitting into four equal parts as the nuts ripen. This unique ability to produce both multiple nuts per bur and burs with a single nut per bur is not found with wild cultivars. This new cultivar's ability to produce multiple nuts per bur occurs approximately 20% of the time, and this ability is steady and consistent with F1 and F2 generations. This unique ability to produce more than one nut per bur increases the annual nut yield of this new cultivar.

Figure 3:
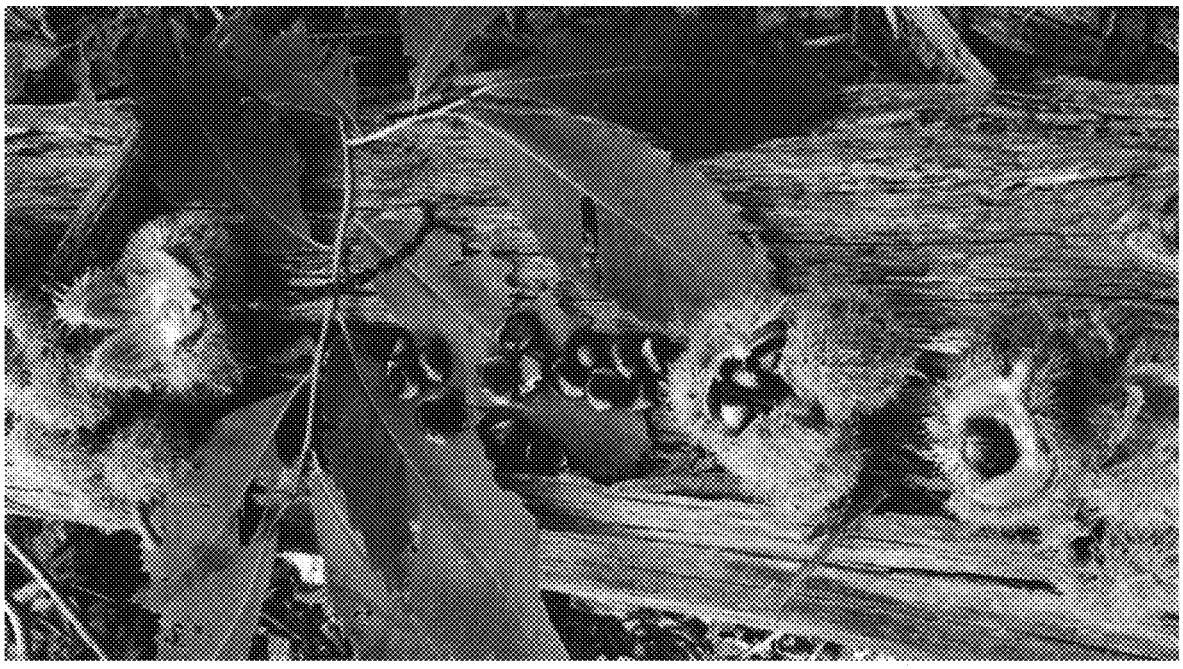
FIG. 3 is a close-up photograph of 'Oz Hunter' with two to six nuts per bur with the nuts displaying flat sides instead of round with burs splitting into four equal parts instead of two.

FIG. 3 provides an up-close view of 'Oz Hunter' with two to six nuts per spiky bur and the nuts displaying flat sides instead of the typical round nut of wild cultivars. The size of the burs with two to six nuts is approximately 25% larger than the single-nut burs the tree produces. Also visible are the spiky burs splitting into four equal parts instead of the two equal splits found on wild Ozark chinquapin trees.

This unique ability to produce not just one nut per bur but also two to six nuts per bur increases this new cultivar's productivity as compared to wild trees. Some of the smaller multiple nuts produced are easily eaten by smaller species of birds that could not normally swallow the larger sized Ozark chinquapin nut. This is significant because the smaller nuts produced by this cultivar can be a food source for smaller birds such as quail, ruffed grouse, woodpeckers and blue jays. Typically, only larger birds such as wild turkeys and crows can eat wild Ozark chinquapin nuts.

The larger nuts produced by American, European and Chinese chestnut are too large for smaller birds and mammals to eat. 'Oz Hunter' produces nuts that are smaller but have a superior flavor, and the smaller nut size is made up for by their concentrated amounts of protein, carbohydrates, unsaturated fats and trace minerals such as magnesium. 'Oz Hunter' nuts have double the protein content of the American chestnut and three to four times more protein than common species of red oak and white oaks. The nuts are the most sought-after food by wildlife in the forest. See Table 1 below.

TABLE 1[3-5]

Protein, Carb., Crude Fat, Pot., Calcium, and Mag. Analysis

| Mast Species | Protein | Carb. | Fat. | Pot. | Cal. | Mag. |
|---|---|---|---|---|---|---|
| 'Oz Hunter' Castanea Ozarkensis | 15.2% | 61.07% | 13.93% | .77% | .15% | .18% |
| White Oak Quercus Alba | 4.6% | 46.60% | 2.90% | .08% | .22% | .05% |
| Scarlet Oak Q. Cocinea | 4.2% | 35.60% | 14.60% | .07% | .18% | .07% |
| American Chestnut C. Dentata | 5-8% | 43.00% | 3-5% | n/a | n/a | n/a |

As noted above, the nuts produced by 'Oz Hunter' are higher in percentage of carbohydrates and proteins compared to all chestnuts. See Table 2 below.

Figure 4:
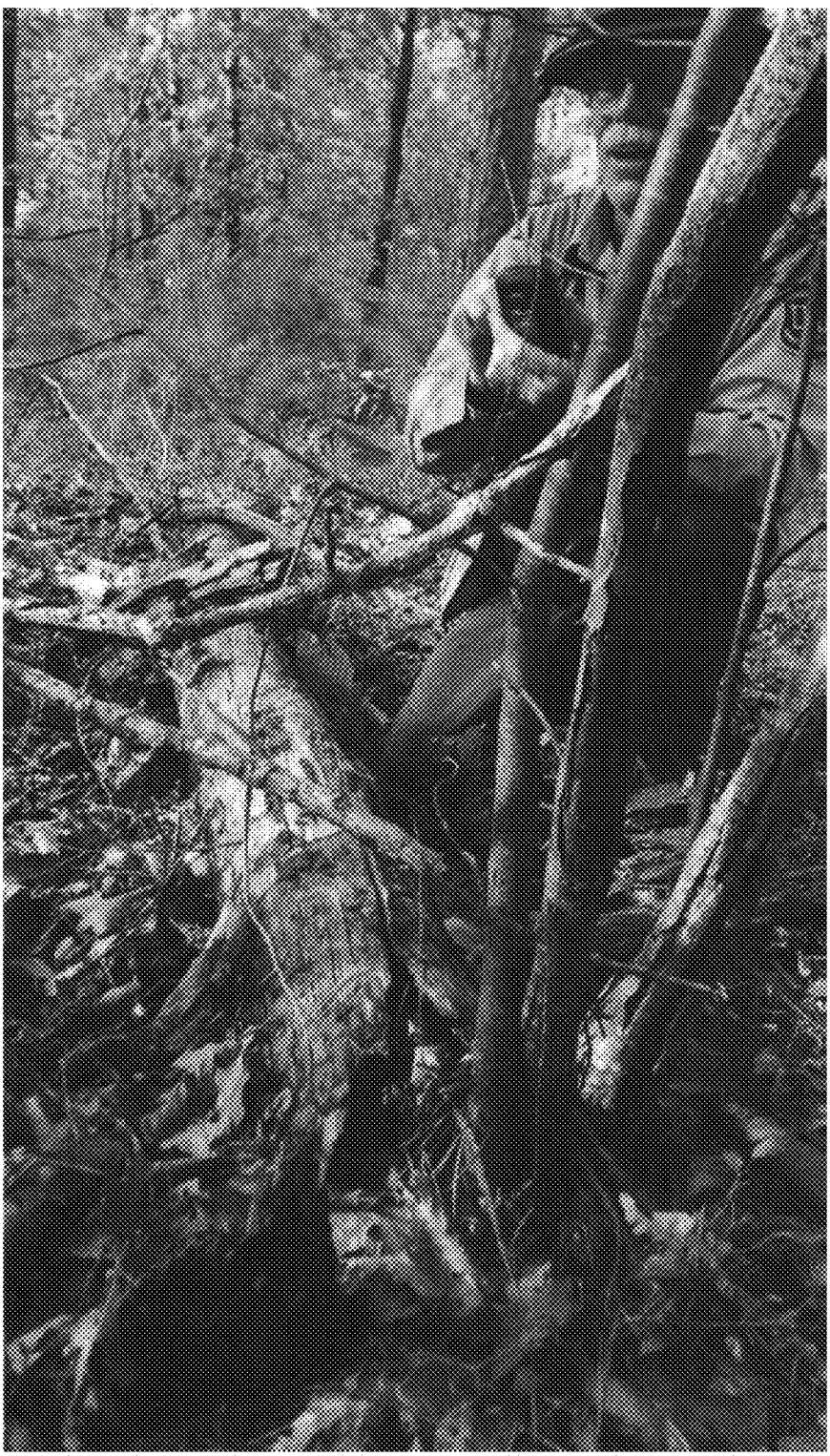
FIG. 4 is a photograph of a typical blighted wild Ozark chinquapin tree killed by the blight with blighted stump sprouts and the old tree trunk.

FIG. 4 is a photo of the now dead trunk of this once heathy wild Ozark chinquapin tree that was killed by the chestnut blight. The microbes in the soil kill the blight fungus so that the fungus only kills above the soil line. For this reason, sometimes (as is visible in this photo) two stems emerge from the still healthy unblighted root system only to die from the blight. In response to the die back of the tree trunk, the roots send up aggressive growing sprouts only to be killed every four to six years by the chestnut blight. The cycle of re-sprout and die back from the blight is typical of remnant populations of wild Ozark chinquapin trees found today. The third sprout that was healthy in the photo will eventually die as well.

In the wild it is extremely rare for an Ozark chinquapin tree to attain a height more than 1.5 feet before it is killed by the chestnut blight. Nut production is almost nonexistent because the tree's ability to reach the upper canopy of the forest and mature has been stopped by the blight. This has left the tree without a seed base to regenerate and rendered the tree functionally extinct.

Figure 5:
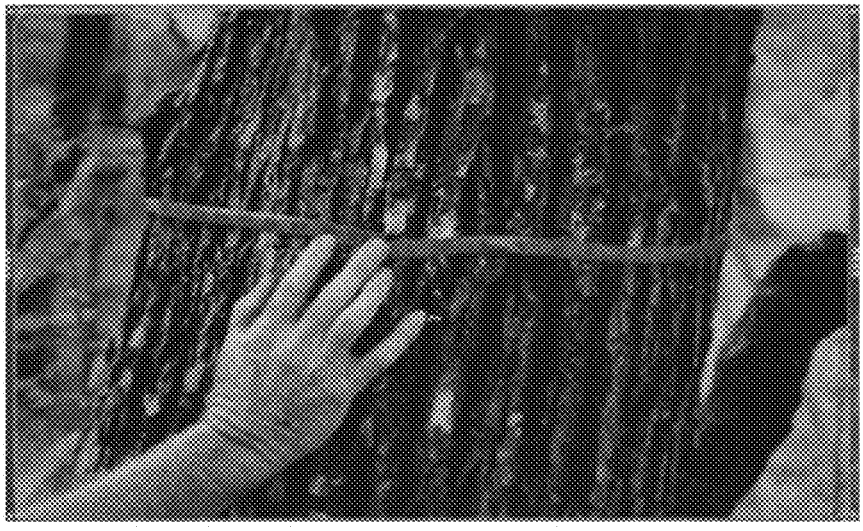
FIG. 5 is a photograph of one of the large blight-free Ozark chinquapin trees used to create 'Oz Hunter'.

FIG. 5 is a photo of one of the rare Ozark chinquapin trees discovered along the edge of a cultivated farm field that exhibited levels of blight resistance and were used to help create 'Oz Hunter'. Wild Ozark chinquapin trees typically become blighted before they attain tree size and exist in the wild in shrub-like instead of as a tree. The tree shown in FIG. 5 is from a photo taken in 1987 when the tree was still alive in rural Clarke County in southwest Arkansas. In 2006 this same tree had already died from the chestnut blight and existed as a blighted stump and sprouts. In February 2006, the inventor collected scion twigs for grafting from these sprouts. Pollen from these grafted twigs and controlled pollination yielded nuts that were planted on the research test plots at Hunter, Mo. Over 99.9% of all surviving Ozark chinquapins die before reaching tree size. Of the 46 rare tree-size Ozark chinquapin trees the inventor found, all eventually died of blight. The tree in FIG. 5 is part of the collections made from blight-tolerant phenotypes used at research test plots at Hunter, Mo. All North American species in the genus *Castanea*, including the Ozark Chinquapin, are susceptible to the chestnut blight. Any resistance to chestnut blight in Ozark chinquapin is extremely uncommon (0.01-0.03%) and is the result of several rare alleles. Blight resistance in chestnuts is quantitative, which means it is the result of multiple genes contributing to the overall resistance of the tree.

Figure 6:
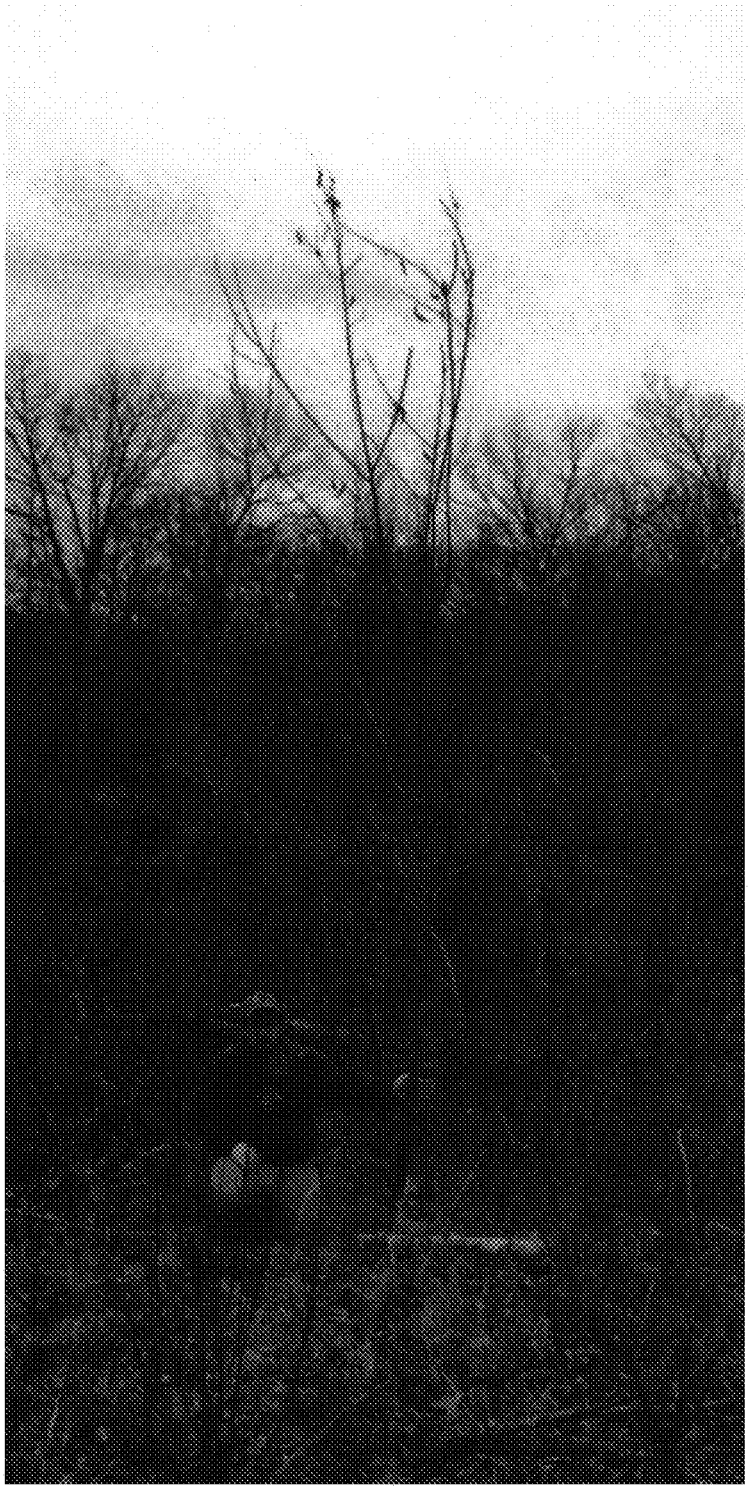
FIG. 6 is a photograph of wild Ozark chinquapin planted in 2009.

FIG. 6 is a photo that was taken on Feb. 19, 2019 of a wild Ozark chinquapin tree planted in the spring of 2009. This ten-year-old tree is 5.7 meters tall with a diameter of 7.0 centimeters at one-meter height. Tree in FIG. 6 is a ten-year-old wild Ozark chinquapin tree planted in the spring of 2009 on research test plot west of Hunter, Mo. No soil amendments or fertilizer were used.

Figure 7:
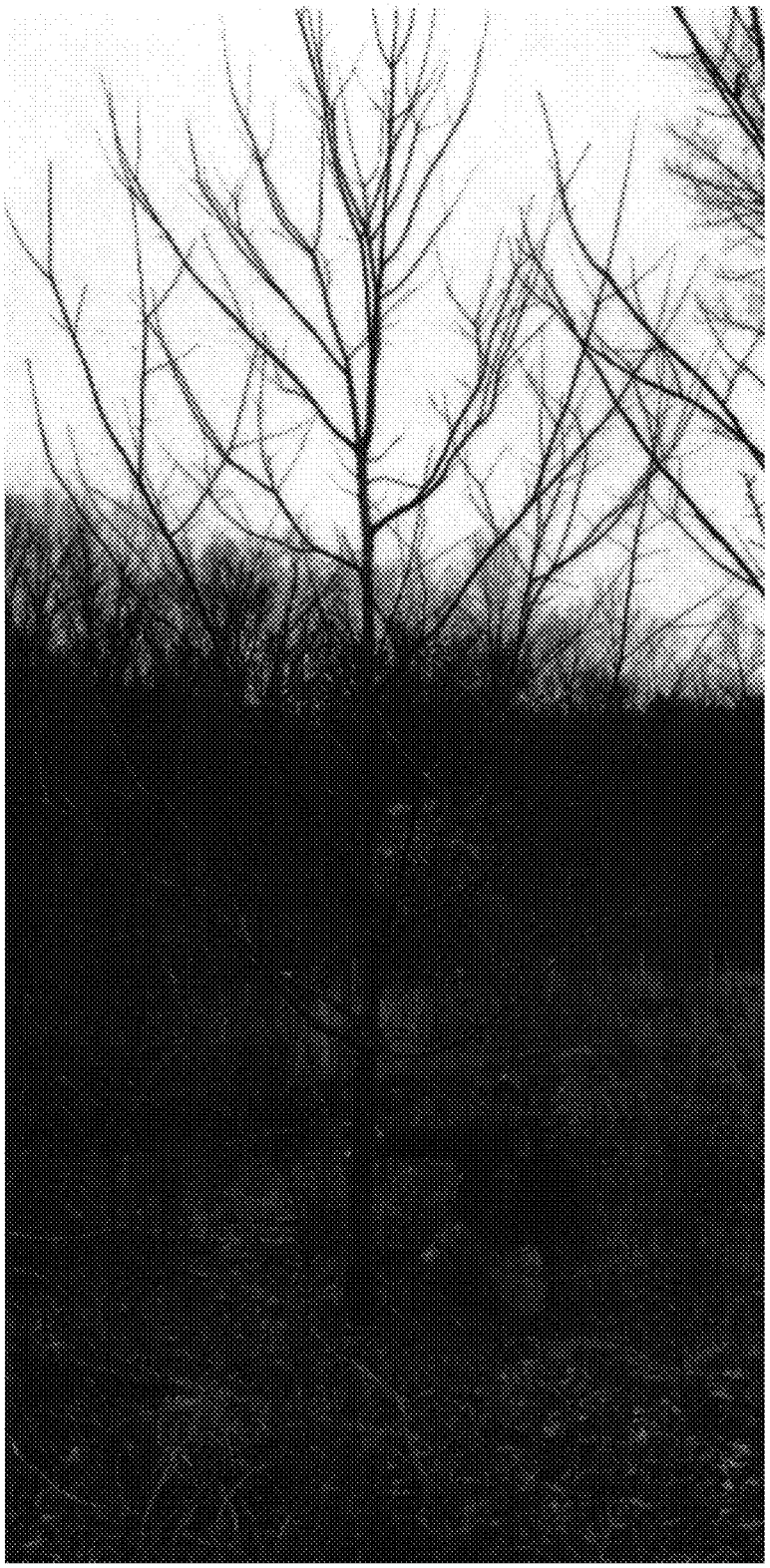
FIG. 7 is a photograph of the crossed tree used to produce 'Oz Hunter' planted in 2009 showing 15-45% more growth than wild Ozark chinquapin.

FIG. 7 is a photo of the crossed tree used to produce 'Oz Hunter' planted in 2009 showing 15-45% more growth than wild Ozark chinquapin. Tree in FIG. 7 is a ten-year-old tree that was planted in the spring of 2009 on a research test plot west of Hunter, Mo. The tree pictured in FIG. 7 is part of the male parentage of 'Oz Hunter'. No soil amendments or fertilizer were used.

Both of the trees in FIGS. 6 and 7 were planted ten meters apart in full sun without the aid of fertilizers or any type of soil amendments or special treatment. 'Oz Hunter' was planted one year after the wild Ozark chinquapin and still achieved more growth.

'Oz Hunter' is precocious with a growth rate 15-45% faster than a typical wild Ozark chinquapin. This rapid growth allows this new cultivar to produce nuts in three to five years as compared to four to seven years average with wild Ozark chinquapin trees, this rapid growth of 'Oz Hunter' is without aid of fertilizer or soil amendments.

Figure 8:
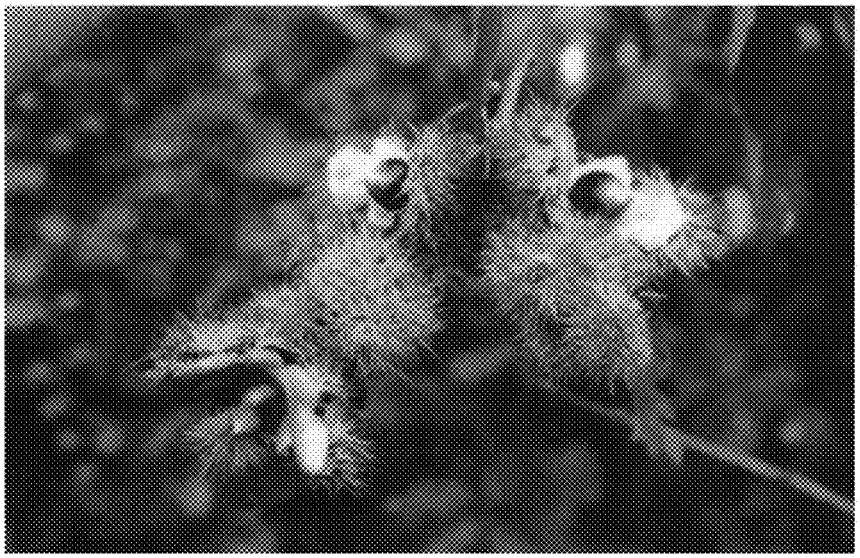
FIG. 8 is a photograph of a typical three to 15 nuts per branch in wild Ozark chinquapin.

FIG. 8 is a rare photo of nut production on a wild Ozark chinquapin tree having three nuts ripening with their spiky burs opening near the end of a branch. If a wild tree manages to live long enough before being blight killed, it typically will produce three to 12 nuts near the end of a branch.

Figure 9:
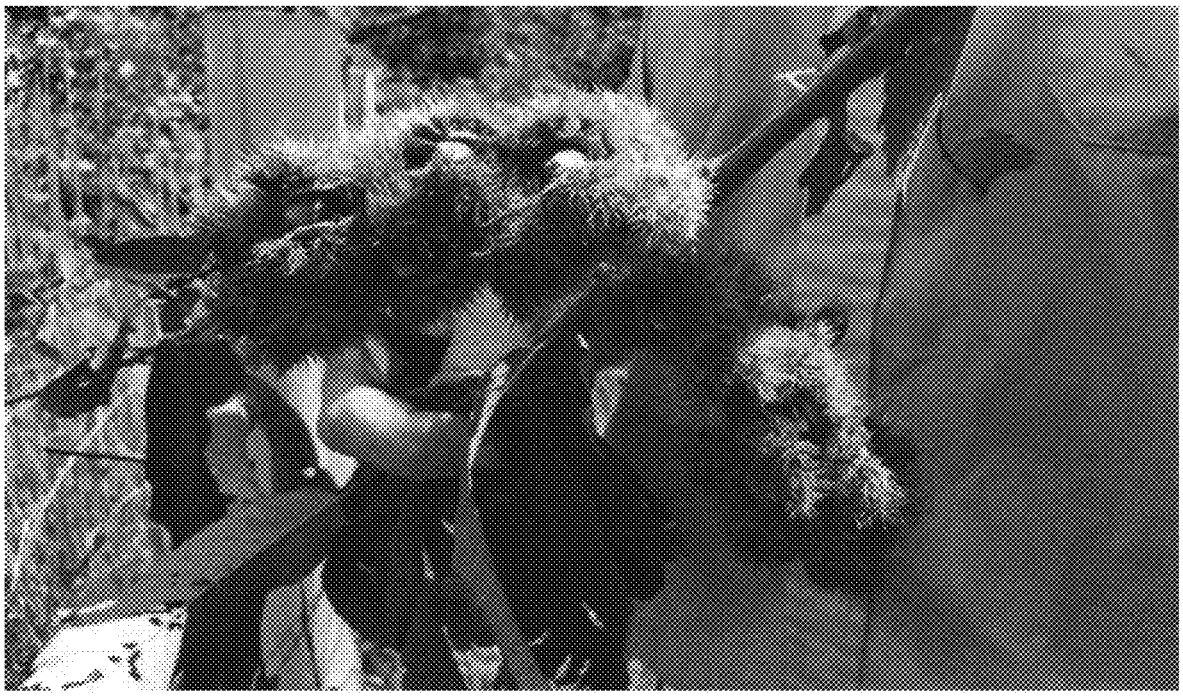
FIG. 9 is a photograph of nut production on 'Oz Hunter' showing up to 47 nuts per branch.

FIG. 9 is a photo showing the higher nut production on 'Oz Hunter' with up to 47 nuts per branch. 'Oz Hunter' has an extremely high nut crop yield.

Figure 10:
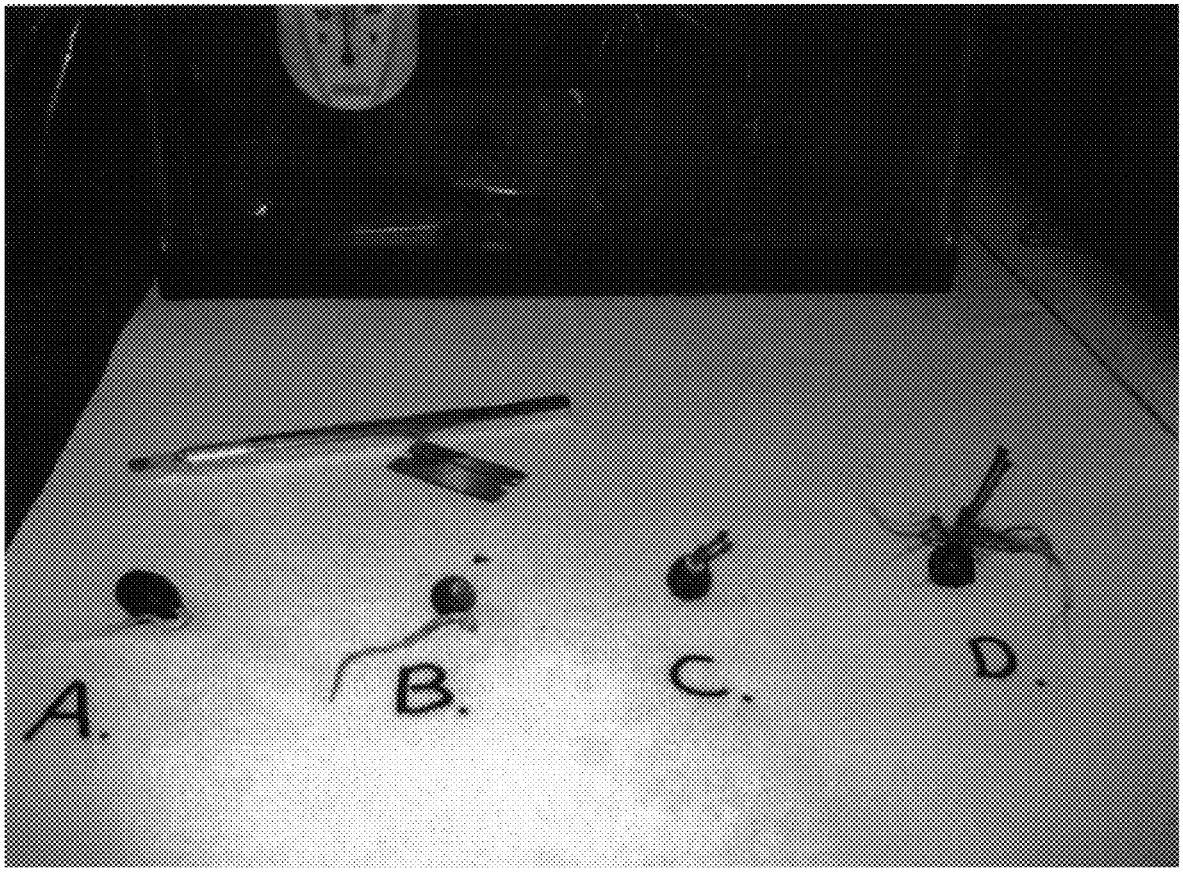
FIG. 10 is a photograph of reproducing Ozark chinquapin twigs grafted onto American chestnut conducted in 2006-2007.

FIG. 10 is a photo of nut grafting first done in February 2007. This method of reproduction allowed production of pollen from remote Ozark chinquapins trees that were hundreds of miles from research test plots. The selected trees from which scion wood was harvested for nut grafting exhibited levels of blight resistance but were difficult to access during pollination. Nut grafting produced clones that produced pollen the first year that was easy to obtain for strategic controlled pollination. Collected pollen was then dried and stored at minus 18 degrees Celcius to be used at a time months or years later.

FIG. 10 illustrates the process of nut grafting, namely:

(A) The process begins with a germinated Ozark chinquapin nut, shown here with the root visible after being kept in cold storage tor five months.

(B) The tap root is cut away with razor blade, and the immature petiole is visible.

(C) A dormant twig collected in February is removed from the tip of a mature branch of a selected Ozark chinquapin tree that will produce pollen. The twig is cut with an X-ACTO™ knife to a taped screwdriver-like bevel shape and carefully inserted into the immature petiole of the nut.

(D) After three to four weeks of keeping the nut grafts at a continuous 18 to 24 degrees Celcius, the dormant twig comes to life, and the buds begin to swell. Later as if it were still on the mature (parent) tree, the twig leaves out and produces pollen.

This time-consuming method requires special attention to detail; watering with an eye dropper four times daily and carefully watering the root ends only so as not to allow any moisture to come into contact with the graft union. This method allowed pollen collection the first year from remote far away trees that were important for the breeding program to produce 'Oz Hunter'.

Figure 11:
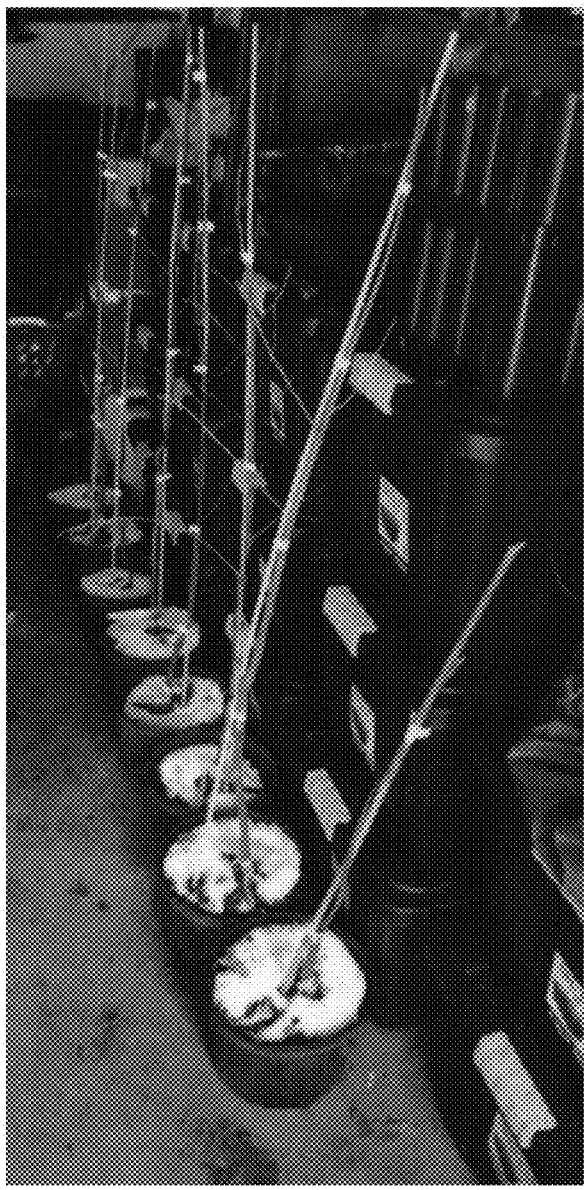
FIG. 11 is a photograph of asexual reproduction using Ozark chinquapin scion wood grafting onto Chinese chestnut *Castanea mollissima* rootstock in 2018.

FIG. 11 is a photo of asexual reproduction using selected Ozark chinquapin and 'Oz Hunter' scion stems grafted onto root stock of Chinese chestnut *Castanea mollissima*. This asexual reproduction method was less time-consuming than nut grafting and accomplished three objectives: controlled pollination could be accomplished without use of lift bucket trucks in remote, roadless hard-to-reach tree locations; the Chinese root stock allowed them to grow in a greater variety of soils; and these grafts serve as a living genetic clone bank of selected trees for the breeding program to produce 'Oz Hunter'.

'Oz Hunter' was created along with controlled pollination from trees found in Missouri, Arkansas, Texas, Oklahoma, Louisiana, Mississippi and Alabama. The methods used to create this new cultivar include field and laboratory observations, plant morphology observations, DNA chloroplast tests, hypovirulence screening and testing, oxalic acid test, blight inoculation stem test, leaf assay blight testing, reproduction using nut, bud and stem grafting, pollen collection, pollen processing, cold storage of pollen and controlled cross pollination. Other research methods performed with this new cultivar include hybridizing, genetically modifying, molecular research testing, clonal propagation, pollinating insects, medical research, micropropagation, use of soil microbes for blight control, air root pruning, inoculation of roots with root production method, building industry use, DNA research, medical use, tanning of animal skins, wood analysis, protein, fats, carbohydrate, cholesterol and trace mineral analysis, air root pruning, food industry use, orchards, agroforestry, livestock food, wood working, soil amendments and terra preta.

REFERENCES

1. Leslie Bost, *Blight Resistance Screening Results*, Missouri Botanical Garden, St. Louis, Mo., May 2019 (ozarkchinquapinmembership.org/blight-screening/).

2. Hannah Carter Pilkey, Ozark Chinquapin Leaf Samples Tolerate Oxalic Acid, SUNY-Environmental Science and Forestry University Laboratory, October 2020 Virtual Meeting (ozarkchinquapinmembership.org/ozark-chinquapin-leaf-samples-tolerate-oxalic-acid-by-hannah-pikley/).

3. Bost, S. H., *Ozark Chinquapin Nutritional Analysis SGS Laboratory*. Unpublished Manuscript (2012).

4. Bonner, F. T., *Seed Biology and Technology of Quercus*. Res. Note SO-183. New Orleans, La.: U.S. Department of Agriculture, Forest Service, Southern Forest Experiment Station (1974).

5. D. Fulbright, Personal Communication (February 2012).

I claim:

1. A new and distinct variety of Ozark chestnut tree named 'Oz Hunter', substantially as illustrated and described herein.

* * * * *

PRIOR ART

PRIOR ART

PRIOR ART

PRIOR ART

PRIOR ART